United States Patent [19]

Ito et al.

[11] 4,421,737

[45] Dec. 20, 1983

[54] PRESSURE-SENSITIVE ADHESIVE TAPE OR PRESSURE-SENSITIVE ADHESIVE SHEET CONTAINING NITROGLYCERIN

[75] Inventors: Toshio Ito, Sekimachi; Hiroshi Ninomiya, Sayama; Kunio Yamagami, Naruto, all of Japan

[73] Assignees: Nippon Kayaku Kabushiki Kaisha; Taiho Pharmaceutical Company Limited; Nichiban Co. Ltd., all of Tokyo, Japan

[21] Appl. No.: 247,307

[22] Filed: Mar. 25, 1981

[51] Int. Cl.³ .......................... A61F 13/02; C09J 7/02
[52] U.S. Cl. ........................................ 424/28; 424/298; 156/334; 427/208.4; 428/352; 428/355; 428/40; 609/897
[58] Field of Search ............... 427/208.4; 156/334; 428/355, 352, 40; 128/268; 424/298, 28

[56] References Cited

U.S. PATENT DOCUMENTS

| | | | |
|---|---|---|---|
| 3,632,740 | 1/1972 | Robinson et al. | 427/208.4 |
| 3,734,097 | 5/1973 | Zaffaroni | 128/268 |
| 3,742,951 | 7/1973 | Zaffaroni | 128/268 |

*Primary Examiner*—Marion McCamish
*Assistant Examiner*—E. Rollins Buffalow
*Attorney, Agent, or Firm*—Oblon, Fisher, Spivak, McClelland & Maier

[57] ABSTRACT

Pressure-sensitive adhesive tapes or sheets containing nitroglycerin whose release and retention are regulated. Process for the production of pressure-sensitive adhesive tapes or sheets containing nitroglycerin, in which a rubber base adhesives applied on a backing is coated with softeners containing nitroglycerin and then covered with an impermeable protection sheet. Process for the production of pressure-sensitive adhesive tapes or sheets containing nitroglycerin, in which a backing is coated with adhesives comprising a rubber base adhesive basis and tackifiers, while a separator is coated with a solution of softeners for rubber base adhesives in which nitroglycerin is dissolved, and then the softener coated surface of the separator is laid on the adhesive-coated surface of the backing and they are kept at the temperature at which nitroglycerin is stable so that the nitroglycerin and softeners transfer into the adhesives.

10 Claims, 2 Drawing Figures

PRESSURE-SENSITIVE ADHESIVE TAPE OR PRESSURE-SENSITIVE ADHESIVE SHEET CONTAINING NITROGLYCERIN

BACKGROUND OF THE INVENTION

This invention relates to adhesive tapes or sheets for medical use and processes for the production thereof, and more particularly to adhesive tapes or sheets containing nitroglycerin in the adhesives which is used for medical treatment for and/or prevention against angina pectoris, myocardial infarction paroxysm and cardiac insufficiently, and processes for the production of such tapes or sheets.

Among internal treatments for ischemic heart disease is vasodilator therapy, and wherein nitroglycerin is used as coronary vasodilator. It is known that nitroglycerin has effects such as dilating of the coronary artery, releasing contracture of the coronary artery and further dilating collateral vessils and resistance vessels, consequently increasing oxygen supply to the ischemic area of cardiac muscle. And also it is known that nitroglycerin has effects such as dilating arteries and reducing the blood pressure throughout the body which leads to reduction of the load being applied to the heart, and at the same time, dilating veins and reducing the amount of venous return which leads to reduction of the forward-load to the heart, and consequently the oxygen consumption in the cardiac muscle is reduced.

Due to the above mentioned effects, nitroglycerin is used for the treatment for heart diseases such as myocardial infarction or angina pectoris.

Conventionally, nitroglycerin was administered by intravenous injection, in the form of sublingual tablets or ointment, and the effect lasting time of each was respectively a few minutes, 20 to 30 minutes, or 3 to 5 hours.

For the treatment for paroxysm from angina pectoris, usually the sublingual tablet containing nitroglycerin is used, but the effect lasting time is short.

When there is necessity to keep up the medical effect of nitroglycerin for long time, for example, in case of the treatment for cardiac insufficiency or the prevention of angina pectoris, an ointment containing nitroglycerin is used. When nitroglycerin is administered in the form of ointment, the ointment prepared by dispersing 2% of nitroglycerin lactose into lanoline-vaseline basis and contained in a tube is generally used. An administering amount of this ointment is determined as follows. At first approximately 1.25 cm of the ointment is pushed out onto a scaled parchment paper applicator (6×9 cm), then applied onto the frontal chest skin and the amount of the ointment is increased by approximately 1.25 cm in each successive time until a headache occurs which is a symptom of side-effect. If this side-effect occurs then the amount of the ointment is decreased. An amount satisfying the purpose of medical treatment and just less than the occurrence of a headache-side-effect, it is considered as the maximum permissible amount or a proper administering amount. In actual use, the ointment is to be pushed out onto a scaled parchment paper in an amount not exceeding that fixed according to the above mentioned manner (generally 2.5 to 5 cm length, the amount of the ointment approximately 0.7 to 1.5 g, the amount of nitroglycerin approximately 14 to 30 mg), and said amount of ointment is to be applied onto the frontal chest skin (the area to be applied onto is usually considered to be 200 cm² or more). In order to avoid the evaporation of nitroglycerin and to prevent the ointment from staining clothes, the ointment-applied part of the body is to be covered with plastic film (e.g. polyvinyliden chloride film which is commercially available under the trade name of "Saran Wrap") which is to be fixed by adhesive tapes. In order to remove the applied ointment, it is necessary to wash with a lukewarm aqueous solution of soap or remove it by gauze containing alcohol. As mentioned above, the use of ointment is troublesome, and it is very difficult to determine an exact amount to be used accurately. Further, as other ways of administering nitroglycerin, there were suggested the ways such that micro capsules or absorbent mediums carrying nitroglycerin therein are dispersed into adhesives or combined with cataplasm or plaster. However, the above mentioned administering ways are not practical. Since there is required a step of putting nitroglycerin into capsules or a step of forming absorbent mediums, the preparation process is troublesome. And according to usual production process of cataplasm or plaster, there is a danger that nitroglycerin explodes.

Recently, a plaster containing nitroglycerin was published (Japanese Patent Laid-Open No. 2604/1980). However, in this adhesive plaster is not improved to obtain suitable retention and release of nitroglycerin.

SUMMARY OF THE INVENTION

For effective prevention or cure of heart disease, adhesive tapes or sheets containing nitroglycerin must be able to release suitable amounts of the nitroglycerin as well as, be capable of retaining the contained nitroglycerin over an extended period of time. In addition, in order to sustain an industrially stable supply of such products, a hazard-free manufacturing process must be developed.

The purpose of this invention is to provide an adhesive tape or sheet (containing nitroglycerin) which can highly retain nitroglycerin in a stable state as well as continuously release it.

This invention embodied in the pressure-sensitive adhesive tape or sheet described hereunder will satisfy the above mentioned purpose.

1. Pressure-sensitive adhesive tape or sheet containing nitroglycerin comprising a nitroglycerin-impermeable backing coated with pressure-sensitive adhesives comprising
   (1) 100 parts by weight of rubber base adhesive basis,
   (2) 20 to 200 parts by weight of at least one kind of tackifier selected from the group consisting of tackifiers with polar groups and those without polar groups,
   (3) 0 to 50 parts by weight of at least one kind of softener selected from the group consisting of softeners with polar groups and those without polar groups,
   (4) the total amount of the tackifiers with polar groups and the softeners with polar groups being 3 to 200 parts by weight, and
   (5) 1 to 10% by weight of nitroglycerin to the whole amount of the adhesives.

2. Pressure-sensitive adhesive tape or sheet containing nitroglycerin comprising a nitroglycerin-impermeable backing coated with pressure-sensitive adhesives comprising
   (1) 100 parts by weight of rubber base adhesive basis,
   (2) 80 to 125 parts by weight of at least one kind of tackifier selected from the group consisting of tackifiers with polar groups and those without polar groups, (3) 0 to 50 parts by weight of at least one kind of softener selected from the group consisting of softeners with polar groups and those without polar groups, (4) the total amount of the tackifiers with polar groups and the softeners with polar groups being 25 to 125 parts by weight, and (5) 1 to 10% by weight of nitroglycerin to the whole amount of the adhesives.

In addition to the essential ingredients described in the above, the pressure-sensitive adhesive tape or sheet may contain various kinds of auxiliary ingredients usually used in adhesives for pressure-sensitive adhesive tapes or sheets.

Furthermore, in accordance with the present invention, a pressure-sensitive adhesive tape or sheet containing nitroglycerin can be produced by coating a backing with rubber base adhesives to form a pressure-sensitive adhesive tape or sheet, applying on the surface of adhesive coating a coat of a solution of softener for rubber base adhesives; wherein nitroglycerin is dissolved or a coat of an ointment containing nitroglycerin, and covering said coating of the softener or the ointment with an impermeable protection sheet, and then keeping thus prepared adhesive tape or sheet at the temperature at which nitroglycerin is stable so that adhesive tape or sheet is aged and thus nitroglycerin transferred together with the softener or ointment to the adhesives.

According to another production process of this invention, pressure-sensitive adhesive tapes or sheets containing nitroglycerin can be produced by coating a release paper with an adhesive comprising a rubber-base adhesive basis, tackifier, nitroglycerin, and if desired, a softener and then covering the surface of adhesive coating with a backing.

DETAILED DESCRIPTION OF THE PREFERRED EMBODIMENTS OF THE INVENTION

Natural and/or synthetic rubber can be as rubber base adhesive basis used in the present invention.

As examples of synthetic rubber that can be used, there can be recited synthetic rubber of isoprene base, isobutylene base and styrene base. In other words, synthetic rubber of any kind can be used, as far as it can be used as a basis of pressure-sensitive adhesives and it does not produce any unfavorable action as a material for nitroglycerin products.

As tackifiers with polar groups, natural rosin with abietic acid as its main element and glycerin ester and pentaerythritol ester of hydrogenated rosin, can be used. As tackifiers without polar groups, poly-β-pinene resin and so-called petroleum-base tackifiers produced by polymerizing petroleum cracking fractions (mainly $C_5$ to $C_9$ cracking fractions) can be used.

Since tackifiers with polar groups have affinity for nitroglycerin, adhesives obtained by mixing tackifiers having polar groups with rubber base adhesive basis having little affinity for nitroglycerin can be adjusted by regulating the combination rate of the two ingredients so that they can have appropriate degree of nitroglycerin release. The combination rate of tackifier with polar group to 100 parts by weight of rubber base adhesive basis is about 20 to 200 parts by weight or more preferably about 50 to 130 parts by weight. Further, more preferable combination rate of tackifiers with polar groups to 100 parts by weight of rubber base adhesive basis is about 80 to 125 parts by weight.

Since substances with or without polar groups can be used as tackifiers, mixtures of both kinds can be used.

Petroleum-base tackifiers of alicyclic structure without polar groups have less affinity for nitroglycerin and adhesives consisting of such resin and rubber are inferior in retention of nitroglycerin, so that nitroglycerin in them leaches on the surface of adhesives as if they were polyvinylchloride combined to a plasticizer with less compatibility. Thus, tackifiers of this kind are not suitable to be used. However, their nitroglycerin release can be controlled by mixing tackifiers without polar groups and tackifiers with polar groups. Usually by mixing 100 parts by weight of tackifiers without polar groups with about 20 parts by weight or more of tackifiers with polar groups, or more preferably about 50 to 200 parts by weight of tackifiers with polar groups, and combining about 20 to 200 parts by weight of said mixture (wherein is contained 3 parts by weight or more of tackifiers with polar groups) or more preferably approximately 50 to 120 parts by weight of said mixture (wherein is contained 17 to 80 parts by weight of tackifiers with polar groups) with 100 parts by weight of rubber, adhesive basis, the adhesive property and the nitroglycerin release can be controlled.

In the present invention, softeners with or without polar groups can be used as ingredients of adhesives. Adhesives containing softeners demonstrate excellent initial adhesion. As softeners without polar groups, mineral oil, polybutene and vaseline, and as softeners with polar groups, long chain fatty acid ester such as isopropyl myristate, ispropyl lanolate and the like, fats and oils, hydrogenated fats and oils, such as hydrogenated castor oil and the like, lanoline or its derivatives, such as purified lanoline, hydrogenated lanoline, lanoline alcohol, lanoline acetate and the like, fatty acid monoglyceride such as glycerin monostearate and the like, and resin having low softening point such as methylester of hydrogenated rosin and the like can be used. Since a softener consisting of isopropyl lanolate alone, in which nitroglycerin is dissolved, does not make a homogeneous coating on a separator for release, then nitroglycerin contained in the softener disperses unhomogeneously into adhesives as well. However, a softener consisting of isopropyl lanolate and hydrogenated lanoline makes a homogeneous coating on a separator for release, and therefore nitroglycerin contained therein disperses homogeneously into adhesives. Thus produced adhesive tapes or sheets is preferable because of the homogeneous release of nitroglycerin. The common combination rate of softeners to 100 parts by weight of rubber base adhesive basis is 0 to 100 parts by weight, preferably about 5 to 50 parts by weight. In this invention, the combination rate of the total amount of tackifiers with polar groups and softener with polar groups to 100 parts by weight of rubber base adhesive basis for adjusting the balance of retention and release of nitroglycerin is about 3 to 200 parts by weight, preferably about 20 to 130 parts by weight and more preferably about 25 to 125 parts by weight. Furthermore, it is appropriate to use softeners without polar groups among aforementioned softeners, for instance polybutene and vaselin, or use softeners with polar groups like lanolin, rosin-ester with low softening point, in order to regulate nitroglycerin release by polar groups in tackifiers to a subtle degree. For this purpose, softeners with nitroglycerin can be used as well.

In this invention, adhesives can contain fillers if desired. The kind of fillers can be the same as those used traditionally for adhesives for ordinary adhesive tapes, provided that they do not accelerate decomposition of nitroglycerin and they have mild acidity. Since kaolin and clay are fillers indicating mild acidity, they are strong in absorbing nitroglycerin. So they can be used to regulate nitroglycerin release.

In the invention, the mixture rate of fillers to 100 parts by weight of rubber base adhesive basis is 0 to about 200 parts by weight, more preferably 0 to about 120 parts by weight.

In this invention, adhesives can contain antioxidants to prevent qualities of rubber base adhesive basis from being degradated on standing. Phenol derivatives such as butyl hydroxy toluene can be used as antioxidants. The amount of antioxidants to the whole amount of adhesives is usually 0 to 2% by weight and more preferably approximately 1% by weight.

When tackifiers with polar groups are used, the favorable combination of ingredients of adhesives in this invention is as follows: rubber base adhesive basis is 100 parts by weight; tackifiers with polar groups are about 20 to 120 parts by weight; those without polar groups are 0 to about 120 parts by weight; fillers are 0 to about 100 parts by weight; softeners are 0 to about 50 parts by weight (and if necessary about 1% by weight of antioxidants to the whole amount of adhesives); and nitroglycerin is about 1 to 10% by weight to the whole amount of adhesives.

In using tackifiers without polar groups, the combination rate is, for example, as follows: rubber base adhesive basis 100 parts by weight; tackifiers without polar groups about 20 to 120 parts by weight; fillers about 20 to 120 parts by weight; softeners with polar groups about 5 to 50 parts by weight; 0 to 2% by weight or preferably about 1% by weight of antioxidants to the whole amount of adhesives; and about 1 to 10% by weight of nitroglycerin.

Nitroglycerin-contained adhesive tapes or sheets of the present invention are made by coating nitroglycerin-contained adhesive, so that they have nitroglycerin-contained adhesive of adequate thickness on the backing of adhesive tapes or sheets, in other words, so that they have a certain amount of nitroglycerin on a certain area of them.

As backing for adhesive tapes of the present invention, all the backings that can be used as backings for ordinary adhesive tapes, that do not have nitroglycerin permeated, and especially that do not give any bad effect on nitroglycerin such as inhibiting its release. Examples which can meet the conditions mentioned above include polyolefin, polyester, polyvinylchloride paper and cloth. From the view point of stability of nitroglycerin, films of polyolefin such as polyethylene and polypropylene are the most suitable as backings.

Nitroglycerin-contained tapes may be rolled. However, they had better be of sheet form with their adhesion surfaces covered with separator for release in order to prevent changes on standing caused by volatilization of nitroglycerin. In the case of sheeted adhesive, it is desirable to seal up them in aluminium packs.

It is favorable as separators for release to have a property to prevent nitroglycerin combined in adhesives from transferring into separators on standing. Plastic films like polyester, polyethylene and polypropylene are suitable as such separators for release. Among them, films of polyolefin such as polyethylene and polypropylene are more desirable. However, even the latter kind of separators can be used as satisfactory ones only after they are given the release treatment like silicone coating. If separators are used only to temporarily protect the adhesion surface, polyethylene-laminated paper with silicone coating on the surface, used for common labels, adhesive products for seals and a part of medical tapes, can be used. On the other hand, when separators need to protect the adhesion surface for a certain duration, such paper is unappropriate because nitroglycerin included in adhesives migrates to paper on standing, resulting in the reduced quantity of nitroglycerin.

Since nitroglycerin is a material for explosives and it is the most dangerous and explosive among various explosives, the maximum care is needed in treating it to secure safety. Therefore, even when it is used as an explosive, it is absorbed by nitrocellulose (in the case of smokeless powders), by diatomaceous earth (in the case of dynamite) and so on.

In addition, though nitroglycerin is relatively stable at 50° C. and under, it is so sensitive to shocks and frictions as to readily explode and is also volatile. By reason of this, transportation of nitroglycerin as a single substance is banned.

Thus, in the production of nitroglycerin-contained tapes or sheets, sufficient care is necessary for safety and changes of the amount of nitroglycerin contained caused by volatilization in the process.

Taking such problems into consideration, the inventors improved the production method of adhesive tapes so as to secure high safety, inhibit volatilization of nitroglycerin, and effectively produce nitroglycerin-contained tapes and sheets.

Generally speaking, production methods of adhesive tapes are roughly devided into the calender coating method, the hot melt coating method, the solution coating method and the emulsion coating method. Since nitroglycerin is very explosive, all the above mentioned methods except the solution coating method are not suited for the production of adhesive tapes or sheets of the present invention. But the improved one of the conventional solution coating method was found to be suitable to produce adhesive tapes or sheets of the present invention.

Both the calender coating method and the hot melt coating method are the ones to apply melted adhesives at the high temperature. In the former method, adhesives need to be prepared suitable for the method. For this purpose, adhesives are prepared first by masticating rubber, then adding thereto tackifiers, fillers and softeners, and finally kneading homogeneously. In this case, open rolls, kneaders, internal mixers etc. can be used. However, whatever machines are used, adhesives of high viscosity (usually several thousands to several tens of thousands poises) are kneaded at the high temperature (usually 90° to 120° C.) under the high shear rate ($1 \times 10^3$ to $5 \times 10^3$/sec). In this method, as adhesives are hot-rolled between several steel hot rolls and frictions caused by the difference of circumference speed of rolls spread adhesives over basic cloth, the method is too likely to make nitroglycerin explosive and volatile in the processes of preparing adhesives and coating them to treat explosive substances like nitroglycerin. So this method cannot be adopted as a production method of nitroglycerin-contained tapes.

In the case of the hot melt coating method, though substances with high thermoplasticity is added to adhesives and adhesives are used with the low viscosity (usually several hundred to several thousand poises), then temperature is as high as 120°–180° C. usually. Moreover, since adhesives are coated at the high velocity, the shear rate is raised (usually $5 \times 10^5$ to $1 \times 10^5$/sec). Thus, this method can never be applied as a production method of tapes containing a extremely dangerous substance, nitroglycerin.

With regard to the emulsion coating method, various problems are involved. Firstly, unless nitroglycerin is emulsified stably, its droplets are brought about, which are very dangerous. Secondly, it is fairly hard to form stable emulsion of nitroglycerin-contained adhesives because nitroglycerin itself is unstable in alkalinity. Thirdly, since the high temperature of over 100° C. and the high calorie are required to dry water, a medium, nitroglycerin volatilizes, which makes the quantitative coating hard, and volatilized nitroglycerin endangers safety.

In the solution coating method, the combination of nitroglycerin is easy because it can be usually treated as the solution in an organic solvent of low concentration in dissolving the components of adhesives in a solvent. According to this method, though the high temperature of 60°–100° C. is usually needed in drying coated materials, the heating method by conduction, which is a longer-time low-temperature method without hot heat, can be applied. If this heating method is used, despite of volatilization of nitroglycerin to some extent, it enables the production of nitroglycerin-contained tapes to be put into practice. In this case, care is necessary for regular repairs to prevent condensation of volatilized nitroglycerin into the blastpipe. Other than above mentioned methods, an example of combining volatile, explosive substances like nitroglycerin with adhesives is explained in this invention. That is, first on the adhesion surface of tapes coated with adhesives in advance, a softener (nitroglycerin-contained), which is super in compatibility with adhesives, is coated. Then after protecting the surface with a separator or something else, it is aged for an adequate duration, usually for several days to diffuse nitroglycerin in adhesives homogeneously.

In this method, adhesive tapes are produced by the ordinary production method. As adhesives for tapes or sheets in this invention, rubber base adhesives are desirable, considering the balance between retention and release of nitroglycerin.

On the surface of adhesives, certain quantity of nitroglycerin homogeneously dissolved in a softener used for adhesives, or for example, the 10% nitroglycerin soluble (including ointment) with refined lanolin as a main element, is coated and aged. This process diffuse and dissolve softeners and nitroglycerin in adhesives. In this case, on the adhesive surface may be put a separator which was previously coated with a solution or ointment containing nitroglycerin. By this method, since nitroglycerin-contained materials are not heated at all and the adhesive surface is covered with a separator or a polyethylene film and laminated immediately after coating, nitroglycerin is prevented from volatilizing.

Nitroglycerin-contained adhesive tapes or sheets produced in the above mentioned manner have the following effects. In the case of using acrylic base adhesives consisting of general acrylic ester copolymer as adhesives, release of nitroglycerin is not sufficient. For instance, when the dissolve test of nitroglycerin to the saline solution containing phosphate buffer (pH 6.0) was conducted at 37° C., the dissolve rate was only 18% after 60 minutes passed. In the test when the tape piece of $5 \times 7$ cm$^2$ (measured nitroglycerin content 2.8 mg) was applied on normal human subjects, no reactions were recognized. On the other hand, in this invention, the dissolve test of adhesives, containing 100 parts by weight of natural rubber and 100 parts by weight of glycerin ester of hydrogenerated rosin or in other words a tackifier with polar groups, to the saline solution containing phosphate buffer (pH 6.0) phisiological salt solution was conducted. Then the dissolve rate was about 73% after 60 minutes passed. When the tape piece of $5 \times 7$ cm$^2$ (measured nitroglycerin content 2.5 mg) was applied on normal human subjects, nitroglycerin's action, that is mild headache was observed one hour later.

Since nitroglycerin tapes or sheets in the invention are stable in dissociation by reservation, the amount of nitroglycerin in adhesives is homogeneous as well as quantitative. Thus, if the required dose is determined, the decision of applying area is easy, which ensures the easiness of overall usage. These tapes or sheets are convenient as well because stripping the applied sheet is the only thing to do when the treatment must be suspended due to adverse reactions etc.

One of the great advantages of this invention is that nitroglycerin can be effectively released from specially composed adhesives. The use of polyolefin films or others as tape basis whose permeability for nitroglycerin is small, prevent nitroglycerin from volatilization almost perfectly, which has been a defect of ointment. In addition, as the tapes or sheets have the promoting effect on percutaneous absorption due to sealing, only 30–60 cm$^2$ of the applied area of the tape by the invention or 2–5 mg of nitroglycerin can result in sufficient effect whereas the equivalent effect can be obtained by over 100–200 cm$^2$ of the applied area of conventional ointment or 14–30 mg of nitroglycerin. And the tape of this invention has advantages such that the duration of medical effects thereof is over 8 hours after the application, the stability on standing of nitroglycerin is excellent, there is no danger of explosions from the impact and accordingly it has a high safety.

The present invention is further illustrated by the following examples, which are not limitative of the present invention.

EXAMPLE 1

10 g of masticated natural rubber (pale crepe), 10 g of glyceride of hydrogenated rosin (Staybelite ester No. 10 produced by HERCULES Incorporated) as tackifier with polar groups, 2.5 g of polybutene (HV-300 produced by NIPPON PETROCHEMICALS CO., LTD.) as softener without polar groups and 0.1 g of butyl hydroxy toluene as antioxidant are stirred and dissolved in a solvent consisting of 85 g of n-hexane and 15 g of toluene. Then, 9.04 g of solution of ethyl acetate wherein nitroglycerin is dissolved and its concentration is 5% is added and stirred well. And thus obtained solution is applied onto a silicone-treated surface of a polypropylene film having a thickness of 90μ which is previously silicone-treated in the manner such that the amount of solid applied onto the silicone-treated surface is 40 g/m$^2$, then the solvent is gradually volatilized. To one side of the film is given the mat-finished, and onto the other side is applied a corona-treated surface of a corona-treated polyethylene film having a thickness of 80μ. And the adhesives is transferred. Sheets containing nitroglycerin with the polypropylene film as the separator and the polyethylene film as the backing are produced according to the above mentioned process.

After these sheets are cut into a given size, they are sealed in the bags of aluminum laminated polyethylene films and preserved. The content of nitroglycerin in these nitroglycerin-contained sheets is about 8 mg/100 cm$^2$. When they are used, the necessary amount of the sheet is cut and the maximum space of the sheet which does not cause adverse reactions like a headache is applied to the chest skin etc.

When the small pieces of the sheets with the space of 1 cm$^2$ each were applied to three normal human subjects and the amount of remaining nitroglycerin in pieces was quantified after certain hours, the result was as follows: one hour later 97% of the initial content in average; 2 hours later 90%; 4 hours later 76% and 8 hours later 61%. In this case, when the initial content is taken as 100%, the differences between that and other figures indicate the percutaneous absorption rate.

When the piece of the sheet of 5×7 cm$^2$ (The measured nitroglycerin content was 2.4 mg.) was applied to the left upper arm of the normal subject, about one hour later the subject complained about a mild headache. But the headache was so mild that the test did not have to be suspended and the headache remained at the same intensity even after the piece was applied for 8 hours.

EXAMPLE 2

10 g of masticated natural rubber (pale crepe), 5 g of rosin glycerin ester as the tackifier with polar groups (Ester gum AAG manufactured by Arakawa Chemical Industries), 7.5 g of the tackifier of petroleum base saturated alicyclic structure without polar groups, (Arkon P-100 made by Arakawa Chemical Industries) and 0.1 g of butylhydroxy toluene as the antioxidant were stirred and dissolved in the solvent of the mixture of 80 g of n-hexane and 10 g of toluene. Then 9.04 g of the toluene solution with 5% nitroglycerin was added to the above mentioned solvent, was stirred well, was coated onto the silicon-treated surface of 65μ thick aluminum laminated polyethylene film so that the amount of solid material was 40 g/m$^2$, and the solvent was volatized gradually. After this, the corona treated surface of 80μ thick polyethylene film was put onto the adhesive surface and adhesives were transferred. Then nitroglycerine-contained sheets (The nitroglycerin content was 8 mg/100 cm$^2$) with the aluminum laminated polyethylene film as the separator and the polyethylene film as the backing were made.

After these sheets were cut into a given size, they were sealed in the bags of aluminum laminated polyethylene and were preserved.

When the small piece of the sheets with the area of 1 cm$^2$ each were applied to three volunteers and the amount of remaining nitroglycerin in pieces was quantified after certain hours, the average remaining rates were as follows: one hour later 95%; 2 hours later 91%; 4 hours later 72%; and 8 hours later 43%. This was an indication of good percutaneous absorption.

When the piece of the sheet of 5×7 cm$^2$ (The measured nitroglycerin content was 2.5 mg.) was applied to the left chest of the normal subject, the subject started to complain about a mild headache 30 minutes later. When six hours passed, the headache and palpitation became so severe that the piece was removed. The fact demonstrates that the release of nitroglycerin by the sheet was so effective that smaller area of sheet pieces can provide sufficient effect in the practical treatment.

EXAMPLE 3

10 g of lightly masticated synthetic isoprene rubber (Kraprene IR-10; manufactured by Kuraray Co., Ltd.), 8 g of glyceride of hydrogenated rosin as tackifier with polar groups and 0.1 g of butyl hydroxy toluene as antioxidant were stirred and dissolved in the solvent of mixture of 90 g of n-hexane and 10 g of toluene. This adhesive was coated onto the silicone-treated surface of 80μ thick aluminum-laminated polyethylene film and dried afterward so that 32 g/m$^2$ of the solid coating would be secured.

Next 10% nitroglycerin ointment with hydrogenated lanolin as the main component was uniformly coated onto the surface of above-mentioned adhesive at the thickness of 8 g/m$^2$. Immediately after that treatment, the adhesive surface of the sheet was covered with the corona-treated surface of 80μ thick polyethylene film the other side of which was mat-finished. This was kept at the temperature of 40° C. and aged in five days.

Lanolin ointment was uniformly transferred into the adhesive and the adhesive layer was transferred to the polyethylene film. Thus the nitroglycerin-contained polyethylene sheet (The content of nitroglycerin was 8 mg/100 cm$^2$.) with the aluminum-laminated separator was obtained. This sheet was cut into the given size and was sealed and wrapped in the aluminum-laminated polyethylene sheet.

The remaining amount of nitroglycerin was quantified through the test on these sheets after given time; after one hour, 96%, after two hours, 89%, after four hours 85%, after eight hours, 64%.

This sheet cut into 5×7 cm$^2$ size (2.7 mg of nitroglycerin was measured to be in.) was applied on the upper part of the left arm of a normal subject. After 1½ hours he complained of mild headache but not to the extent that this test should be suspended. Even after eight hours there was no major change of the symptom.

EXAMPLE 4

8 g of masticated natural rubber (pale crepe) and 2 g of polyisobutylene rubber (Vistanex LMMH manufactured by Esso Chemicals) were mixed. 10 g of glyceride of hydrogenated rosin as tackifier with polar groups (Stebelite Ester No. 10 manufactured by Hercules Company), 2.5 g of refined lanolin as softening agent with weak polar groups and 0.1 g of butyl hydroxy toluene were stirred and dissolved in the mixture of solvent made of 85 g of n-hexane and 15 g of toluene. Next 9.04 g of ethyl acetate solution containing 5% nitroglycerin was added and stirred well with the above-mentioned mixture. This was applied as the solid element to the 60μ thick silicone-treated surface of silicone-treated polypropylene film at the rate of 40 g/m$^2$. After that the solvent was gradually volatilized and on this surface the corona-treated surface of 80μ thick one-side corona treated polyethylene film was attached. By transferring adhesive polyethylene film-based sheet containing nitroglycerin (Nitroglycerin content was 8 mg/100 cm$^2$) with the polypropylene film as liner was obtained. This sheet was cut into given size and sealed and preserved in the aluminum-laminated polyethylene film bag.

The result of the medical effectiveness of the sheet was as good as that of above-mentioned Example 3.

EXAMPLE 5

10 g of masticated natural rubber (pale crepe), 4 g of tackifier with polar groups (Ester Gum-H manufactured by Arakawa Chemical Industries), 4 g of saturated alicyclic petroleum base resin with non polar group (FTR-6100 manufactured by Mitsui Petrochemical Industries, Ltd.) and 0.1 g of butyl hydroxy toluene as antioxidant were stirred and dissolved in the mixture solvent made of 90 g of n-hexane and 10 g of toluene.

This adhesive was applied to the silicon-treated surface of silicone-treated polyethylene laminated liner so that the solid material would be applied at the rate of 32 g/m$^2$ and dried afterwards. On this adhesive surface the corona-treated surface of 80$\mu$ thick corona-treated polyethylene film with the mat treatment on the other side was attached and a polyethylene sheet with separator was made.

Next while the separator of this polyethylene sheet was removed, 10% nitroglycerin ointment with hydrogenated lanolin as the principal ingredient was applied to the adhesive surface at the rate of 8 g/m$^2$. Immediately after this it was covered with the silicone-treated surface of 65$\mu$ thick silicone-treated aluminum laminated polyethylene film. This was kept aging in the temperature of 40° C. for five days. Thus polyethylene-based nitroglycerin-contained sheet (Nitroglycerin content was 8 mg/100 cm$^2$) with aluminum laminated polyethylene film as separator was produced.

After cutting this sheet into the given size, it was sealed and preserved in the aluminum laminated polyethylene bag.

The remaining amount of nitroglycerin was quantified through the test on these sheets: after one hour 96%, after 2 hours 93%, after four hours 88%, after eight hours 65%. When this sheet of 5×7 cm$^2$ size (with the measured nitroglycerin content of 2.8 mg) was applied to the upper part of the left arm of a normal subject, he complained of a mild headache after one hour, but not to the extent that would require the suspension of the test. After eight hours this piece was removed.

EXAMPLE 6

8 g of masticated natural rubber (pale crepe) and 2 g of styrene-isoprene thermoplastic rubber (Kraton TR-1107 manufactured by Shell Chemical Co.) were mixed. 4 g of pentaerythritol ester of hydrogenated rosin (Pentalyn-H manufactured by Hercules Co.) as tackifier, 6 g of petroleum base alicyclic tackifier without any polar groups (Quinton D-100 manufactured by Nippon Zeon Co.), 2.5 g of polybutene (HV-300 manufactured by Japan Petrochemical Co.) as softening agent and 0.1 g of butyl hydroxy toluene as antioxidant were stirred with 90 g of n-hexane and dissolved together. Next was added 9.04 g of toluene solution with 5% nitroglycerin in it and stirred well together. This was applied to silicone-treated surface of 65$\mu$ thick aluminum-laminated polyethylene film so that the rate of solid element would be 40 g/m$^2$. This film after the above application was placed with the adhesive surface upward on the heated plate of approximately 40° C. and solvent was volatilized gradually. Corona-treated surface of 80$\mu$ thick polyethylene film, one side of which was given corona-treatment, was attached to it and by transferring adhesive agent polyethylene-based nitroglycerin contained sheet (Nitroglycerin content was 8 mg/100 cm$^2$) with aluminum laminated polyethylene film as separator was produced. After cutting this sheet into given size, it was sealed and preserved in the aluminum laminated polyethylene bag.

The result of medical effect was as good as that of above example 5.

EXAMPLE 7

10 g of masticated natural rubber (pale crepe), 10 g of petroleum base alicyclic tackifiers without polar groups (Escorez 1202-U manufactured by Esso Chemicals), 2.5 g of refined lanolin as the softener containing a little quantity of ester group as a polar group, and 0.1 g of butyl hydroxy toluene as the antioxidant were stirred and dissolved in the solvent of the mixture of 85 g of n-hexane and 15 g of toluene. Then 9.04 g of 5% nitroglycerin-ethyl acetate solution was added and stirred well to prepare the adhesive solution.

Next, the above mentioned adhesive solution was coated onto the silicone treated surface of 90$\mu$ thick polypropylene film so that the amount of solid material was 40 g/m$^2$, the solvent was volatilized gradually, then the adhesive surface was attached to the corona treated surface of 80$\mu$ thick polyethylene film the other side of which was mat-finished, and adhesives were transferred. Then nitroglycerin contained sheet (The nitroglycerin content was 8 mg/100 cm$^2$.) with the polyethylene film as the backing and the polypropylene film as the separator were made. After these sheets were cut into a given size, they were sealed in the bags of aluminum-laminated polyethylene and were preserved.

The remaining amount of nitroglycerin was quantified through the test on these sheets; one hour after the application 93%; 2 hours later 88%; 4 hours later 70%; and 8 hours later 35%. The result indicated good percutaneous absorption. When the piece of the sheet of 5×7 cm$^2$ (The measured nitroglycerin content was 2.5 mg.) was applied to the left upper arm of the normal subject, the subject started to complain about a headache 20 minutes after the application. 3 hours after the application, the headache and palpitation got so worse that the test was suspended. The fact demonstrates that smaller area of sheet pieces can provide sufficient effect.

EXAMPLE 8

10 g of synthetic isoprene rubber (Kraprene IR-10 manufactured by Kuraray Co., Ltd.) and 10 g of kaolin clay (NN Kaolin produced by Tsuchiya Kaolin) were masticated. Then together with these two, 8 g of poly-$\beta$-pinene resin as tackifier without polar groups (Piccolite S-100 manufactured by Esso Chemicals), 4.5 g of refined lanolin as softener with weak polar groups and 0.1 g of butyl hydroxy toluene as antioxidant were stirred and dissolved in the solvent of the mixture of 90 g of n-hexane and 10 g of toluene. Then 13.04 g of the 5% nitroglycerin-toluene solution was added to the above mentioned solution, was stirred well, was coated onto the silicone treated surface of 90$\mu$ thick polypropylene film so that the amount of solid material was 40 g/m$^2$, and the solvent was volatilized gradually. Furthermore, the adhesive surface was covered with the corona treated surface of 80$\mu$ thick polyethylene film the other side of which was mat-finished and adhesives were transferred. Then nitroglycerin-contained sheets (The nitroglycerin content was 8 mg/100 cm$^2$.) with the polyethylene film as backing and the polypropylene film as separator were made. After these sheets were cut into a given size, they were sealed in bags of aluminum laminated polyethylene and were preserved.

The results of the test on effect of the sheet were as favorable as those in Example 7.

EXAMPLE 9

10 g of masticated natural rubber (pale crepe), 10 g of tackifiers with polar groups (Ester gum-H manufactured by Arakawa Chemical Industries), 2 g of refined lanolin as softener with the small amount of polar groups, 0.5 g of white vaseline as softener without polar groups and 0.1 g of butyl hydroxy toluene as antioxidant were stirred and dissolved in the solvent of the mixture of 90 g of n-hexane and 10 g of toluene. Then 9.04 g of the 5% nitroglycerin-ethyl acetate solution was added to the above mentioned solvent, was stirred well, was coated onto the silicone treated surface of 90μ thick aluminum-laminated polyethylene film so that the amount of solid material was 40 g/m$^2$, and the solvent was volatilized gradually. After this, the adhesive surface was covered with the corona treated surface of 80μ thick polyethylene film the other side of which was mat-finished and adhesives were volatilized gradually. Then nitroglycerin-contained sheets (The nitroglycerin content was 8 mg/100 cm$^2$.) with the polyethylene film as backing and the aluminum-laminated polyethylene film as separator were made. After these sheets were cut into a given size, they were sealed in bags of aluminum-laminated polyethylene and were preserved.

The remaining amount of nitroglycerin was quantified through the application test of the sheets: one hour after the application 94%; 2 hours later 88%; 4 hours later 76%; and 8 hours later 57%. When the piece of the sheet of 5×7 cm$^2$ (The measured nitroglycerin content was 2.6 mg.) was applied to the left chest of the normal subject, the subject started to complain about a mild headache about 20 minutes after the application. But the headache was so mild that the test was not suspended until it turned to be too severe 6 hours later.

Figure 1:
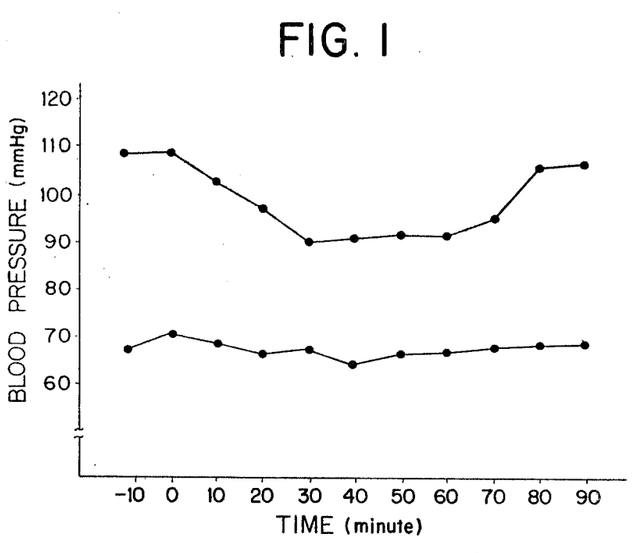
FIG. 1 shows changes of blood pressure when sheets containing nitroglycerin according to the present invention are applied.
Figure 2:
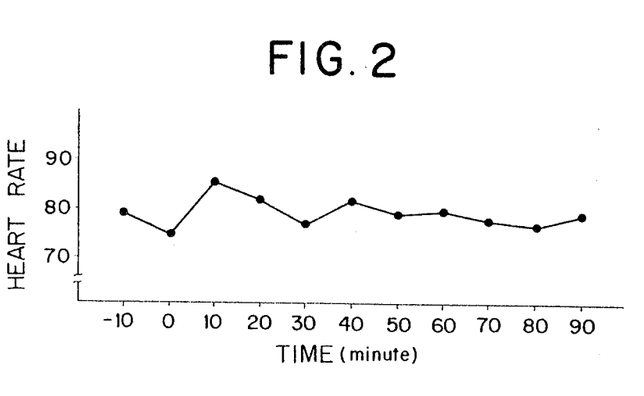
FIG. 2 shows changes of heart rate when sheets containing nitroglycerin according to the present invention are applied to human bodies.

The changes in blood pressure and heart rate of the normal subject applied with the sheet are shown in FIGS. 1 and 2. The horizontal axis in the two figures indicates the passage of time in minutes, the vertical one in FIG. 1 the blood pressure in mmHg, and that in FIG. 2 the heart rate in count/min.

The test was conducted by applying the sheet piece of 7×10 cm$^2$ (The nitroglycerin content was 5.4 mg.) for 60 minutes. In other words, when the time was zero minute, the piece was applied and when that was the 60 minute's point, it was removed. Approximately 10 minutes after the piece was applied, the palpitation of the subject got severe. Though 30 minutes from the start the subject complained about a mild headache, his palpitation and headache disappered about 20 minutes after the piece was removed. It was also observed that percutaneous absorption of nitroglycerin lowered the systolic pressure and raised the heart rate.

At the same time as the above mentioned test, the electrocardiogram (ECG) was recorded (lead II). Almost no changes in ECG were brought about by reason of the piece.

Therefore, it was proven that the sheet is suitable for the treatment and prophylaxis of heart diseases if the applied area of the sheet is adequately chosen.

EXAMPLE 10

Stability Test on Nitroglycerin

The stability test of nitroglycerin was conducted, in which the nitroglycerin was contained in the sheets produced according to examples mentioned above, which were sealed and preserved in aluminum packs. Its stability was fairly good as shown in Table 1. By the way, the preservation conditions were as in the table.

TABLE 1

| Examples | Preservation conditions (Initial Content is 100%) | |
|---|---|---|
| | 37° C. One month after | 50° C. One month after |
| 1 | 98 | 95 |
| 2 | 100 | 97 |
| 3 | 99 | 96 |
| 4 | 102 | 99 |
| 5 | 97 | 95 |
| 6 | 96 | 94 |
| 7 | 103 | 98 |
| 8 | 94 | 90 |
| 9 | 98 | 96 |

EXAMPLE 11

Test on Effect and Pharmacology

By using a beagle anesthesized with pentobarbital, changes in hemodynamics were researched with applying nitroglycerin contained tapes (The size was 7×10 cm$^2$. The nitroglycerin content was 2.6 mg.) produced according to the example 9 to the subject.

The beagle was 9.8 kg heavy. The tape in the example 9 was applied to the dog's left chest shaved with a razor for 90 minutes. The result is shown in Table 2.

According to the findings, the systolic blood pressure, the pressure in the left ventricle and that in the right atrium were reduced while the blood flow in the coronary artery was raised 15 minutes after the tape was applied. Such changes disappeared 60 minutes after the tape was removed. In other words, it was demonstrated that applying the sheets produced by the invention was effective on ischemic heart diseases by reducing the preloading and postloading on the heart, alleviating the job of the heart and increasing the coronary blood flow.

TABLE 2

| | | Before application | After application (min) | | | | | | After release (min) | |
|---|---|---|---|---|---|---|---|---|---|---|
| | | | 15 | 30 | 45 | 60 | 75 | 90 | 30 | 60 |
| Blood pressure | Systolic blood pressure | 160 | 141 | 130 | 135 | 135 | 135 | 135 | 140 | 160 |
| | Diastolic pressure | 85 | 80 | 75 | 80 | 80 | 80 | 80 | 85 | 85 |
| Heart rate | (beats/min) | 176 | 176 | 176 | 184 | 184 | 184 | 184 | 176 | 176 |
| Cardiac minute volume | (ml/min) | 1000 | 950 | 925 | 950 | 950 | 950 | 950 | 1050 | 1050 |
| Right atrial pressure | (mm H$_2$O) | 10 | 6 | 4 | 8 | 8 | 8 | 8 | 12 | 10 |
| Left intra atrial pressure | (mmHg) | 167 | 145 | 130 | 135 | 135 | 135 | 135 | 147 | 147 |
| Coronary artery blood flow | (ml/min) | 25 | 30 | 35 | 35 | 35 | 35 | 35 | 35 | 31 |

TABLE 2-continued

|  |  | Before application | After application (min) | | | | | | After release (min) | |
| --- | --- | --- | --- | --- | --- | --- | --- | --- | --- | --- |
|  |  |  | 15 | 30 | 45 | 60 | 75 | 90 | 30 | 60 |
| Vertebral artery blood flow | (ml/min) | 50 | 70 | 75 | 65 | 65 | 65 | 65 | 50 | 45 |
| Urinary volume | (ml/15 min) | 0.90 | 0.85 | 0.80 | 0.80 | 0.80 | 0.80 | 0.80 | 0.80 | 0.80 |

EXAMPLE 12

Clinical case—Prophylaxis of Spontaneous Angina Pectoris

The case is a 45-year-old male. He sometimes experienced 5 minute-lasting dull pains under the sternun between 1:00 a.m. to 5:00 a.m. since four years ago. This phenomenon has broken out frequently since one year ago and pains have been spread to the shoulder and chin. When the maximum permissible dosage of the nitroglycerin contained sheet (In this case, the sheet was 5×6 cm². Its nitroglycerin content was 2.2 mg.) obtained in Example 9, instead of the calcium antagonist, was applied to the left chest of the patient at the bedtime, it could block fits almost perfectly.

EXAMPLE 13

Clinical case—Treatment of Angina of Effort

The maximum permissible dosage of the nitroglycerin contained sheets (In this case, the size of the sheet was 5×8 cm². Its nitroglycerin content was 3.0 mg.) obtained in Example 6 was applied on the left chest of the case, a 58-year-old male with about 5 fits of angina a week. After applying this, the Graded Exercise Test (GET) was conducted. Before the application, chest pains were recognized with 1.5 mm-ST-reduction and the endurable duration of GET was 300 seconds. On the contrary, three hours after the application, ST reduction was only 1.0 mm and the endurable duration of GET 705 seconds. Five hours after, the former was 0.8 mm and the latter 685 seconds. Therefore after the application of the sheet, the great improvement in ST reduction and increase in exercise capacity was seen.

What is claimed is:

1. Pressure-sensitive adhesive tape or sheet containing nitroglycerin comprising a nitroglycerin-impermeable backing coated with pressure-sensitive adhesives comprising:
   (1) 100 parts by weight of rubber base adhesive basis selected from the group consisting of natural rubber, synthetic isoprene rubber, isobutylene rubber, styrene-butadiene rubber, styrene-isoprene thermoplastic rubber, a mixture of natural rubber and isobutylene rubber, a mixture of natural rubber and styrene-isoprene thermoplastic rubber, and a mixture of synthetic isoprene rubber and kaolin clay,
   (2) 20 to 200 parts by weight of at least one kind of tackifier selected from the group consisting of tackifiers with polar groups and those without polar groups,
   (3) 0 to 50 parts by weight of at least one kind of softener selected from the group consisting of softners with polar groups and those without polar groups,
   (4) the total amount of the tackifiers with polar groups and the softeners with polar groups being 3 to 200 parts by weight, and
   (5) 1 to 10% by weight of nitroglycerin to the whole amount of the adhesives.

2. Pressure-sensitive adhesive tape or sheet containing nitroglycerin comprising a nitroglycerin-impermeable backing coated with pressure-sensitive adhesives comprising:
   (1) 100 parts by weight of rubber base adhesive basis selected from the group consisting of natural rubber, synthetic isoprene rubber, isobutylene rubber, styrene-butadiene rubber, styrene-isoprene thermoplastic rubber, a mixture of natural rubber and isobutylene rubber, a mixture of natural rubber and styrene-isoprene thermoplastic rubber, and a mixture of synthetic isoprene rubber and kaolin clay,
   (2) 80 to 125 parts by weight of at least one kind of tackifier selected from the group consisting of tackifiers with polar groups and those without polar groups,
   (3) 0 to 50 parts by weight of at least one kind of softener selected from the group consisting of softners with polar groups and those without polar groups,
   (4) the total amount of the tackifiers with polar groups and the softeners with polar groups being 25 to 125 parts by weight, and
   (5) 1 to 10% by weight of nitroglycerin to the whole amount of the adhesives.

3. Pressure-sensitive adhesive tape or sheet according to claim 1 or claim 2 in which the tackifier with polar groups is selected from the group consisting of rosin, hydrogenated rosin, rosin ester, hydrogenated rosin ester and maleic modified hydrocarbon resin.

4. Pressure-sensitive adhesive tape or sheet according to claim 1 or claim 2 in which the tackifier without polar groups is selected from the group consisting of alicyclic hydrocarbon resin, hydrogenated hydrocarbon resin and poly-$\beta$-pinene resin.

5. Pressure-sensitive adhesive tape or sheet according to claim 1 or claim 2 in which the tackifier with polar groups is selected from the group consisting of rosin ester and hydrogenated rosin ester, and the softener with polar groups is selected from the group consisting of isopropyl myristate, isopropyl lanolate, purified lanoline and hydrogenated lanoline.

6. Pressure-sensitive adhesive tape or sheet according to claim 1 or claim 2 in which the softener with polar groups is selected from the group consisting of long chain fatty acid ester, lanoline, lanoline derivatives, fatty acid monoglyceride, fats, oils, and resin having low softening point.

7. Pressure sensitive adhesive tape or sheet according to claim 1 or claim 2 in which the softener is selected from mineral oil, polybutene and vaseline.

8. Pressure sensitive adhesive tape or sheet according to claim 1 or claim 2 in which the impermeable backing is selected from polyethylene, polypropylene and polyethylene terephtalate.

9. Pressure sensitive adhesive tape or sheet according to claim 1 or claim 2 which comprises a polyolefin film coated with pressure sensitive adhesives comprising
   (1) 100 parts by weight of natural rubber, synthetic isoprene rubber, isobutylene rubber, styrene-butadiene rubber, styrene-isoprene thermoplastic rubber, a mixture of natural rubber and isobutylene rubber, a mixture of natural rubber and styrene-isoprene thermoplastic rubber or a mixture of synthetic isoprene rubber and kaolin clay,
   (2) 5 to 120 parts by weight of a mixture of 0.5 to 2 parts by weight of tackifier with polar groups consisting of rosin, hydrogenated rosin, rosin ester, hydrogenated rosin ester and maleic modified hydrocarbon resin and 1 parts by weight of tackifier without polar groups consisting of alicyclic hydrocarbon resin, hydrogenated hydrocarbon resin and poly-$\beta$-pinene resin,
   (3) 5 to 50 parts by weight of softener consisting of isopropyl myristate, isopropyllanolate, purified lanoline and hydrogenated lanoline,
   (4) 1 to 10% by weight of nitroglycerin to the whole amount of the adhesive 10. Pressure-sensitive adhesive tape or sheet according to claim 1 or claim 2 in which the softener with polar groups is selected from the group consisting of isopropyl myristate, lanoline fatty acid isopropylate, purified lanoline, hydrogenated lanoline, lanoline alcohol, lanoline acetate, glycerin monostearate, hydrogenated castor oil, and methylester of hydrogenated rosin.

* * * * *

UNITED STATES PATENT AND TRADEMARK OFFICE
CERTIFICATE OF CORRECTION

PATENT NO. : 4,421,737
DATED : December 20, 1983
INVENTOR(S) : Toshio Ito et al

It is certified that error appears in the above-identified patent and that said Letters Patent is hereby corrected as shown below:

On the title page the following should be added:

-- [30] Foreign Application Priority Data

March 25, 1980    Japan    55/36848 --.

Signed and Sealed this

Seventeenth Day of April 1984

[SEAL]

Attest:

GERALD J. MOSSINGHOFF

Attesting Officer    Commissioner of Patents and Trademarks